United States Patent
Ehben et al.

(10) Patent No.: US 7,925,331 B2
(45) Date of Patent: Apr. 12, 2011

(54) APPARATUS FOR DISPLAYING A TISSUE CONTAINING A FLUORESCENT DYE

(75) Inventors: Thomas Ehben, Weisendorf (DE); Sebastian Schmidt, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 159 days.

(21) Appl. No.: 11/525,023

(22) Filed: Sep. 22, 2006

(65) Prior Publication Data

US 2007/0083123 A1   Apr. 12, 2007

(30) Foreign Application Priority Data

Sep. 26, 2005   (DE) .................. 10 2005 045 907

(51) Int. Cl.
*A61B 6/00* (2006.01)
(52) U.S. Cl. ............... 600/473; 600/476; 600/407
(58) Field of Classification Search .......... 600/407, 600/425, 427, 473, 431, 476
See application file for complete search history.

(56) References Cited

U.S. PATENT DOCUMENTS

| | | | |
|---|---|---|---|
| 4,895,431 A | 1/1990 | Tsujiuchi et al. | |
| 5,371,368 A | 12/1994 | Alfano et al. | |
| 6,178,340 B1 * | 1/2001 | Svetliza | 600/310 |
| 6,826,424 B1 * | 11/2004 | Zeng et al. | 600/476 |
| 7,155,274 B1 * | 12/2006 | Wake et al. | 600/476 |
| 7,190,991 B2 * | 3/2007 | Cable et al. | 600/407 |
| 7,328,059 B2 * | 2/2008 | Sevick-Muraca et al. | 600/473 |
| 7,383,076 B2 * | 6/2008 | Ntziachristos et al. | 600/473 |
| 7,616,985 B2 * | 11/2009 | Stearns et al. | 600/473 |
| 7,797,034 B2 * | 9/2010 | Rice et al. | 600/473 |
| 2002/0016539 A1 | 2/2002 | Michaelis et al. | |
| 2004/0010192 A1 * | 1/2004 | Benaron et al. | 600/431 |
| 2004/0249260 A1 * | 12/2004 | Wang et al. | 600/407 |

FOREIGN PATENT DOCUMENTS

| | | |
|---|---|---|
| DE | 37 38 667 A1 | 5/1988 |
| DE | 39 08 928 C2 | 5/1991 |
| DE | 196 23 172 C1 | 10/1997 |
| DE | 197 54 909 A1 | 6/1999 |
| DE | 100 21 431 A1 | 11/2001 |
| WO | WO 2004079444 A2 * | 9/2004 |
| WO | WO 2004081865 A2 | 9/2004 |

* cited by examiner

*Primary Examiner* — Unsu Jung
*Assistant Examiner* — Nigel Fontenot
(74) *Attorney, Agent, or Firm* — Harness, Dickey & Pierce, P.L.C.

(57) ABSTRACT

An apparatus is disclosed for displaying a tissue containing a fluorescent dye at least in sections. It is proposed for the purpose of simplification to record the tissue with a number of cameras from different observation angles while omitting a beam splitter, and subsequently to produce a joint superimposed overall image.

20 Claims, 2 Drawing Sheets

APPARATUS FOR DISPLAYING A TISSUE CONTAINING A FLUORESCENT DYE

PRIORITY STATEMENT

The present application hereby claims priority under 35 U.S.C. §119 on German patent application number DE 10 2005 045 907.2 filed Sep. 26, 2005, the entire contents of which is hereby incorporated herein by reference.

FIELD

The invention generally relates to an apparatus for displaying a tissue containing a fluorescent dye at least in sections.

BACKGROUND

During the surgical removal of a tumor, the problem arises that healthy tissue frequently cannot be distinguished with the naked eye from a tissue affected by a tumor. In order to provide a remedy here, the patient is administered before the operation with a fluorescent dye that is specifically enriched in the tumor. During the operation, the exposed tissue is illuminated with a light in the near infrared region that is suitable for exciting the fluorescent dye. The tissue is recorded with the aid of an image acquisition device that has an optical unit for separating a fluorescent image generated by the fluorescent light, and a native tissue image formed by the ambient light. The recorded fluorescent images and the tissue images are superimposed by means of an image processing device, the tumorous tissue being labeled in the superimposed image by means, for example, of a false color display.

Arranged downstream of an objective in the conventional image acquisition device is a beam splitter that distributes the recorded image over two different channels that are each provided with a camera. One channel is used to record the fluorescent image, and the other channel is used to record the native tissue image. The conventional image acquisition device requires a relatively high outlay on production because, in particular, of the provision of a beam splitter.

SUMMARY

In at least one embodiment, an apparatus is specified that can be produced simply and cost effectively, for displaying a tissue containing a fluorescent dye at least in sections.

According to at least one embodiment of the invention, an apparatus is provided for displaying a tissue containing a fluorescent dye, at least in sections, and which comprises:
a first image acquisition device, arranged at a first observation angle, for acquiring a first fluorescent image and/or a first native tissue image,
a second image acquisition device, arranged at a second observation angle, which differs from the first observation angle, for acquiring a second fluorescent image and/or a second native tissue image, and
an image generating device for generating
(i) a joint fluorescent image reconstructed from the first and the second fluorescent image and having a prescribed common observation angle,
and/or
(ii) a joint tissue image reconstructed from the first and the second native tissue image and having a prescribed common observation angle,
and for superimposing one of the native first or second tissue images or the joint tissue image from one of the first or second fluorescent images or the joint fluorescent image in order to produce an overall image reproducing the tissue from a uniform observation angle.

It is advantageously possible to use the inventive apparatus of at least one embodiment to dispense with an optical system that is expensive to produce, in particular a beam splitter. All that is required, for example, is to provide two cameras with the aid of which the tissue to be displayed is recorded from two mutually differing observation angles. An image can be reconstructed from a uniform observation angle by use of the image generating device proposed by at least one embodiment of the invention, this being done from the images recorded with the two cameras from different observation angles by means of conventional image reconstruction methods. It is possible in this case for both the fluorescent image and the native tissue image to be involved. By superimposing images from the same observation angle, it is possible to generate an overall image in which, for example, a tumor can be distinguished from the surrounding healthy tissue.

According to an advantageous refinement of at least one embodiment, a third image acquisition device is provided for acquiring a third fluorescent image and/or a third native tissue image from a third observation angle. For example, the first and second image acquisition device can be cameras that have a high sensitivity, particularly in the wavelength region >700 nm. To this end, appropriate filters can also be arranged upstream of these acquisition devices. The third image acquisition device can be a camera that is sensitive in the entire wavelength region of visible light.

Such an image acquisition device is suitable, in particular, for producing native tissue images.

The first, second and, if appropriate, third image acquisition device can be combined in a common housing to form a handheld unit. Such a handheld unit can be of relatively compact design, particularly in the case of the use of CCD cameras as image acquisition devices.

The image acquisition device can include a computer with a program, comprising an image processing algorithm, for generating the overall image. Such a program can be used to generate first 2D spatial coordinates on the basis of the first fluorescent image, and second 2D spatial coordinates on the basis of the second fluorescent image, and a first set of 3D coordinates from the first and second 2D spatial coordinates in order to generate a 3D fluorescent image from the common observation angle. A 2D fluorescent image can then be generated from the 3D fluorescent image.

In a similar way, it is also possible to generate third 2D spatial coordinates on the basis of the first native tissue image, and fourth 2D spatial coordinates on the basis of the second native tissue image, and a second set of 3D coordinates from the third and fourth 2D spatial coordinates in order to generate a 3D native tissue image from the common observation angle. A 2D native tissue image can also be generated in this case from the 3D native tissue image. The generation, described above, of the 2D images having a common observation angle is generally known.

The common observation angle can be, expediently, the first, second or, if appropriate, third observation angle. The outlay on producing images can thereby be reduced.

According to a further refinement of at least one embodiment of the invention, a device for projecting a pattern, preferably a grid, onto the tissue is provided. This can, for example, concern a laser suitable for generating a grid. Such a grid can be acquired by the image acquisition devices and be used in reconstructing the common image. It is thereby possible to simplify the reconstruction and carry it out with particular exactitude. The reconstruction of the overall image is, however, also possible without the projection of a pattern. In this case, structures in the tissue can be detected by means of the image processing algorithm by comparison of the images recorded from the different observation angles, and be used as reference for reconstructing an image from a common observation angle.

Such image processing algorithms are based on the theory of central perspective projection.

The 2D native tissue image is superimposed on the 2D fluorescent image in order to generate the overall image. It has proved to be particularly advantageous to acquire the 2D native tissue image by the third image acquisition device, and to use the third observation angle as common observation angle. In this case, a 2D fluorescence image from the third observation angle is generated from the first and the second fluorescent image, and the 2D native tissue image acquired by the third image acquisition device is subsequently superimposed on it. The proposed method requires a relatively low computational outlay, since there is no need for a reconstruction of a native tissue image.

According to a further refinement of at least one embodiment of the invention, the first, second and/or third image acquisition device in each case has one lens that can be focused, preferably automatically. It is thereby possible to focus the image acquisition device automatically onto different prescribed image planes such that fluorescent and/or native tissue images of different image planes can be acquired. Information relating to the position of fluorescence emission centers can also thereby be obtained inside deeper layers of tissue. It is thereby possible, for example, to display the geometric extent of a tumor at least in the layers of tissue located near the surface.

According to a further advantageous refinement of at least one embodiment of the invention, the image generating device can be used to display the fluorescent images of the same image plane with the same color in the overall image by means of a false color display. This renders it possible, for example, for a tumor to be distinguished from a surrounding healthy tissue with particular ease by a viewer.

BRIEF DESCRIPTION OF THE DRAWINGS

An example embodiment of the invention is explained below in more detail with the aid of the drawings, in which.

DETAILED DESCRIPTION OF THE EXAMPLE EMBODIMENTS

Figure 1:
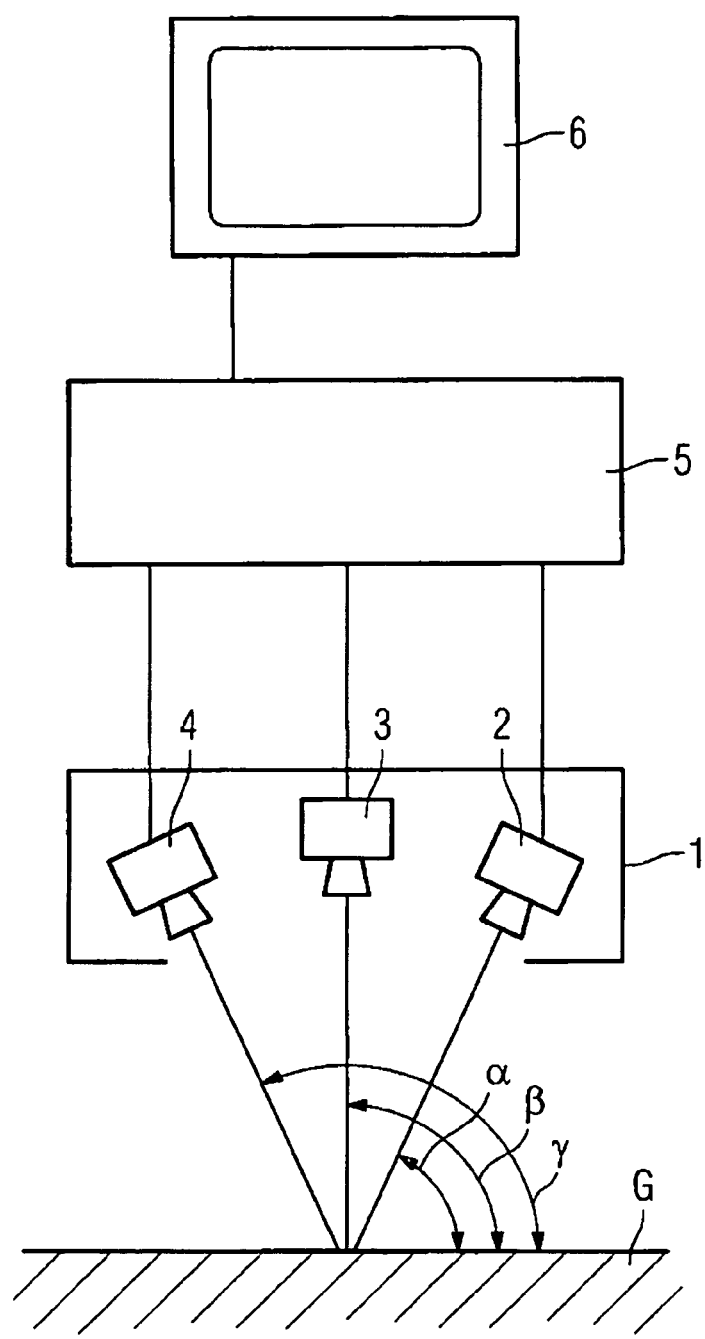
FIG. 1 shows a schematic of an apparatus.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

A first camera 2, a second camera 3 and a third camera 4 are held in a housing 1 in FIG. 1. The cameras 2, 3 and 4 are expediently CCD cameras. The cameras 2, 3, 4 are fitted in the housing 1 such that a tissue G can thereby be recorded simultaneously from different observation angles $\alpha$, $\beta$ and $\gamma$. In this case, the optical axes of the lenses of the cameras 2, 3 and 4 can be arranged in a fashion tilted to one another, or else in a fashion parallel to one another.

The cameras 2, 3 and 4 are connected to an image acquisition device, for example a computer 5. The computer 5 is connected to a monitor 6 for the purpose of displaying the overall images generated.

The first camera 2 and the third camera 4 are provided for the purpose of recording fluorescent images, and the second camera 3 is provided for the purpose of recording native tissue images. To this end, the first camera 2 and the third camera 4 can be CCD cameras with a high sensitivity in the near infrared region, for example a wavelength of more than 700 nm. However, it is also possible to use conventional CCD cameras upstream of which a suitable filter is place, for example. The second camera 2 is sensitive in the entire wavelength region of visible light.

Figure 2:
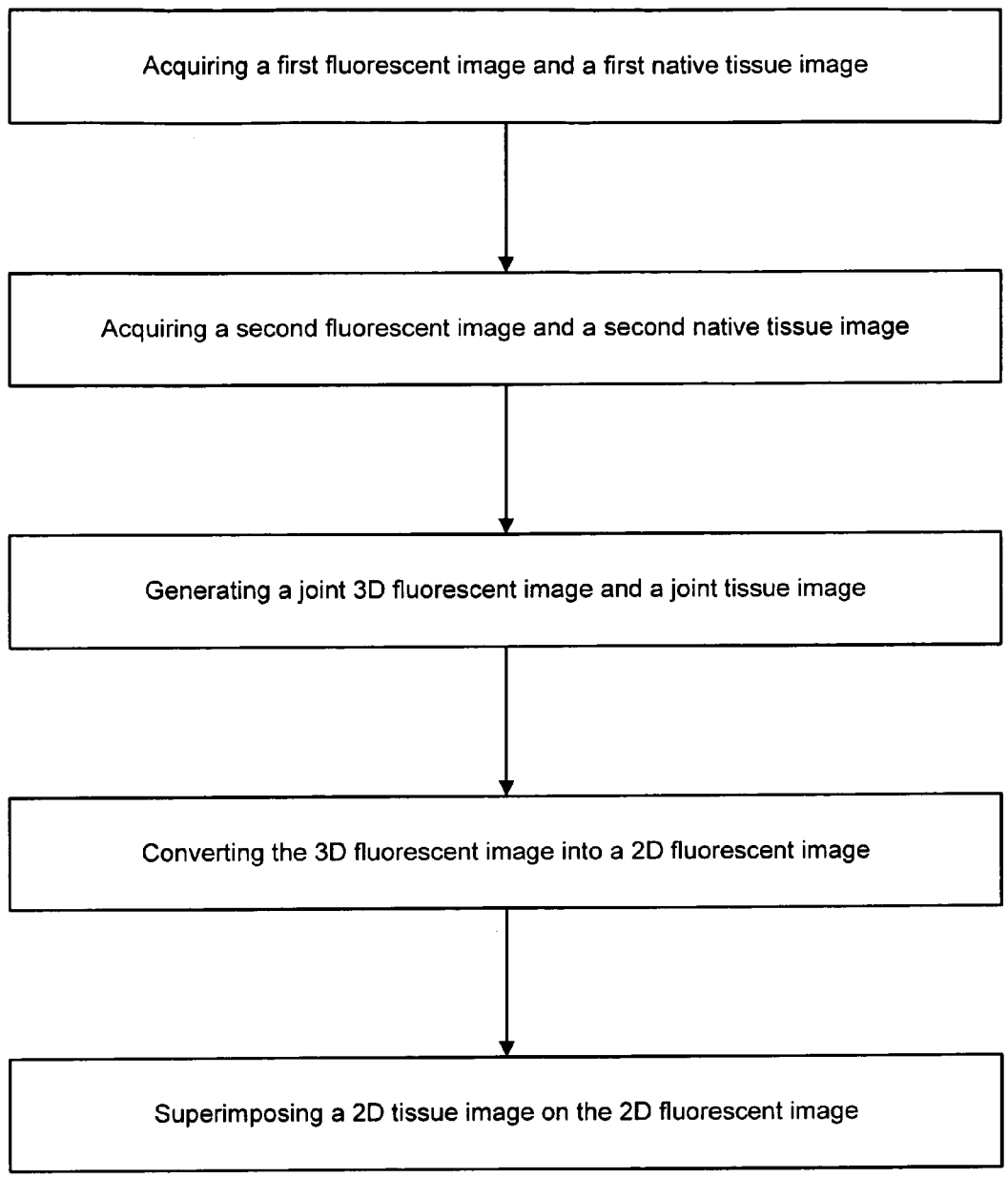
FIG. 2 shows a flowchart for generating an overall image.

The functioning of the apparatus will now be explained in more detail in conjunction with the flowchart shown in FIG. 2.

In order to generate any superimposed overall image composed of a 2D fluorescent image and a 2D native tissue image, a first fluorescent image is recorded with the first camera 2 from the observation angle $\alpha$, and a second fluorescent image is recorded with the third camera 4 from the observation angle $\gamma$. A 3D fluorescent image is produced from the first and the second fluorescent image with the aid of known image processing algorithms in the computer 5. In a following step, a 2D fluorescent image is generated from the 3D fluorescent image from a prescribed observation angle. The prescribed observation angle can expediently be the observation angle $\beta$ of the second camera. The 2D fluorescent image is subsequently superimposed on a native tissue image recorded with the second camera 3. In this case, the 2D fluorescent image can be reproduced in a false color display.

It is, of course, also possible, for example, to use the first camera 2 and the third camera 4 to record native tissue images, and to generate a joint 2D native tissue image therefrom, and subsequently to superimpose a fluorescent image recorded with the second camera 3 thereon.

It addition, it is also possible to provide an apparatus having only two cameras with the aid of which the tissue G can simultaneously be recorded from two different observation angles. In this case, at least one of the two cameras must be suitable both for recording fluorescent images and for recording native tissue images. The generation of an overall image is performed here in a way similar to the above described method, that is to say for example by recording two fluorescent images from different observation angles and generating a 2D fluorescent image under a prescribed common observation angle. Here, the common observation angle can expediently correspond to the observation angle of that camera used to record the 2D fluorescent image to be superimposed.

The proposed apparatus can be produced relatively cost effectively, since it is possible to dispense with a complicated optical system, in particular a beam splitter and the like. The cameras used to produce the apparatus can be conventional CCD cameras. They can, in particular, be provided with a device for automatically focusing the lenses. This simplifies and speeds up the image production.

The proposed apparatus can also be used to make a statement on the vertical distribution of the fluorescent dye in the tissue G, in particular by preparing a joint 3D fluorescent image from a first and a second fluorescent image. For example, it is possible to establish whether the tissue sections contained in the fluorescent dye extend laterally toward the interior of the tissue. Such information can be considered in the false color display of the fluorescent images and can supply the surgeon with valuable indications of the extent of a tumor.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for displaying a tissue containing a fluorescent dye at least in sections, comprising:
    a first image acquisition device, arranged at a first observation angle with respect to the tissue, to acquire a first fluorescent image by illuminating the tissue with a light in a near infrared region utilized for exciting a fluorescent dye and a first native tissue image formed by ambient light;
    a second image acquisition device, arranged at a second observation angle with respect to the tissue differing from the first observation angle, to acquire a second fluorescent image and a second native tissue image; and
    an image generating device to generate,
        a joint fluorescent image reconstructed from the first and the second fluorescent images and including a common observation angle with respect to the tissue, and
        a joint tissue image reconstructed from the first and the second native tissue images and including the common observation angle with respect to the tissue, and
        the image generating device configured to superimpose at least one of the first native tissue image, the second native tissue image and the joint tissue image with at least one of the first fluorescent image, the second fluorescent image and the joint fluorescent image to produce an overall image reproducing the tissue from a uniform observation angle with respect to the tissue.

2. The apparatus of claim 1, further including a third image acquisition device to acquire at least one of a third fluorescent image and a third native tissue image from a third observation angle.

3. The apparatus of claim 1, wherein the first and second image acquisition devices are fitted in a common housing.

4. The apparatus of claim 1, wherein the image generating device comprises a computer with a program, including an image processing algorithm, to generate the overall image.

5. The apparatus of claim 1, wherein first 2D spatial coordinates are generated on the basis of the first fluorescent image, and second 2D spatial coordinates are generated on the basis of the second fluorescent image, and a first set of 3D coordinates is generated from the first and second 2D spatial coordinates to generate a 3D fluorescent image from a third common observation angle.

6. The apparatus of claim 5, wherein a 2D fluorescent image is generated from the 3D fluorescent image.

7. The apparatus of claim 5, wherein third 2D spatial coordinates are generated on the basis of the first native tissue image, fourth 2D space coordinates are generated on the basis of the second native tissue image, and a second set of 3D coordinates is generated from the third and fourth 2D space coordinates to generate a 3D native tissue image from the third common observation angle.

8. The apparatus of claim 7, wherein a 2D native tissue image is generated from the 3D native tissue image.

9. The apparatus of claim 1, further including a device to project a pattern onto the tissue.

10. The apparatus of claim 1, including,
    a 2D native tissue image acquired by a third image acquisition device and
    a 2D fluorescent image generated from a third observation angle with respect to the tissue and the first and second fluorescent images,
    wherein the 2D native tissue image is superimposed on the 2D fluorescent image.

11. The apparatus of claim 10, wherein the third observation angle is used as a third common observation angle.

12. The apparatus of claim 2, wherein at least one of the first, second and third image acquisition devices in each case have one focusable lens.

13. The apparatus of claim 1, wherein the image generating device is usable to display the fluorescent images of the same image plane with a same color in the overall image by way of a false color display.

14. The apparatus of claim 2, wherein the first, second and, third image acquisition devices are fitted in a common housing.

15. The apparatus of claim 1, further comprising a device to project a grid onto the tissue.

16. An apparatus for displaying a tissue containing a fluorescent dye at least in sections, comprising:
    first image acquisition means, arranged at a first observation angle with respect to the tissue, for acquiring a first fluorescent image by illuminating the tissue with a light in the near infrared region utilized for exciting a fluorescent dye and a first native tissue image formed by ambient light;
    second image acquisition means, arranged at a second observation angle with respect to the tissue differing from the first observation angle, for acquiring a second fluorescent image and a second native tissue image; and
    an image generating means for generating,
    a joint fluorescent image reconstructed from the first and the second fluorescent images and including a common observation angle with respect to the tissue, and
    a joint tissue image reconstructed from the first and the second native tissue images and including the common observation angle with respect to the tissue,
    the image generating means further for superimposing at least one of the native first tissue image, the native second tissue image and the joint tissue image from at least one of the first fluorescent image, second fluorescent image and the joint fluorescent image to produce an overall image reproducing the tissue from a uniform observation angle with respect to the tissue.

17. The apparatus of claim 16, further comprising third image acquisition means for acquiring at least one of a third fluorescent image and a third native tissue image from a third observation angle.

18. The apparatus of claim 16, wherein the first and second image acquisition means are fitted in a common housing.

19. The apparatus of claim 17, wherein the first, second and, third image acquisition means are fitted in a common housing.

20. An apparatus for displaying a tissue containing a fluorescent dye at least in sections, comprising:

a first image acquisition device, arranged at a first observation angle with respect to the tissue, to acquire a first fluorescent image by illuminating the tissue with a light in the near infrared region utilized for exciting a fluorescent dye and a first native tissue image formed by ambient light;

a second image acquisition device, arranged at a second observation angle differing from the first observation angle with respect to the tissue, to acquire a second fluorescent image and a second native tissue image; and an image generating means for generating, a joint fluorescent image reconstructed from the first and the second fluorescent images and including a common observation angle with respect to the tissue, and a joint tissue image reconstructed from the first and the second native tissue images and including the common observation angle, and the image generating means further for superimposing at least one of the first native tissue image, the second native tissue image and the joint tissue image with at least one of the first fluorescent image, second fluorescent image and the joint fluorescent image to produce an overall image reproducing the tissue from a uniform observation angle with respect to the tissue.

* * * * *